United States Patent [19]

Williams et al.

[11] 4,237,166
[45] Dec. 2, 1980

[54] 1-ACRYLOYL-3-(SUBSTITUTED) PHENYL UREAS

[75] Inventors: John W. Williams, Waukegan; Frank C. Becker, Gurnee, both of Ill.

[73] Assignee: Abbott Laboratories, North Chicago, Ill.

[21] Appl. No.: 48,414

[22] Filed: Jun. 14, 1979

Related U.S. Application Data

[63] Continuation-in-part of Ser. No. 875,253, Feb. 6, 1978, abandoned.

[51] Int. Cl.$^3$ .................... A01N 37/10; A01N 37/34; A01N 47/28; C07C 101/00
[52] U.S. Cl. ................ 424/310; 260/465 D; 424/304; 424/322; 560/34; 564/46
[58] Field of Search ............ 424/310; 560/34

[56] References Cited

U.S. PATENT DOCUMENTS

| 3,660,484 | 5/1972 | Martin et al. ............... 424/322 |
| 3,793,213 | 2/1974 | Taber et al. ............... 252/107 |
| 3,803,227 | 4/1974 | Joos et al. ............... 260/552 R |

FOREIGN PATENT DOCUMENTS

| 888316 | 8/1953 | Fed. Rep. of Germany ........ 260/55 E |
| 5338277 | 1/1968 | Japan ............... 424/322 |
| 235012 | 11/1967 | U.S.S.R. . | |

*Primary Examiner*—Allen J. Robinson
*Attorney, Agent, or Firm*—Paul D. Burgauer; Robert L. Niblack

[57] ABSTRACT

1-Acryloyl ureas carrying a cyano-, carbamoyl- or carbalkoxy-phenyl group on the 3-position have been found to be highly effective as fungicides when incorporated into or applied to agricultural media, plastics, paints or the like.

15 Claims, No Drawings

1-ACRYLOYL-3-(SUBSTITUTED) PHENYL UREAS

BACKGROUND OF THE INVENTION

This application is a continuation-in-part of our earlier filed application, U.S. Ser. No. 875,253, filed Feb. 6, 1978 now abandoned.

DETAILED DESCRIPTION OF THE INVENTION

Useful agricultural crops, plant life in general, paints, painted surfaces and plastics often are attacked by various types of common fungi. Particularly, fruit and vegetable bearing plants frequently host fungi which may damage the fruit or vegetable to the point where it cannot be marketed and, therefore, drastic reduction in harvest income can result. Also, plastics and painted surfaces used or stored in moist atmospheres are often attacked by fungi which produces unsightly surfaces.

It has now been found that crops of the above nature, plastics, paints and the like can be protected by applying to such substrates a compound of the formula

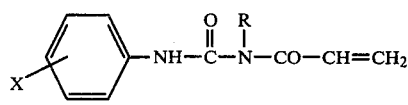

(I)

wherein X represents CN, $CONR_2$ or COOalk wherein each R independently represents hydrogen or alk, and alk stands for a saturated loweralkyl group of 1–3 carbons. These acryloyl ureas are effective at concentrations of 10–5000 ppm and these concentrations are not damaging to the plants or crops themselves, and they do not discolor paints to which they are added or plastics in which they are incorporated rated.

The new compounds of the above formula can be applied directly to paints or plastic formulations or they can be applied to agronomical substrates as solutions or dusts. Sprays are preferably prepared from a water-dispersible or from an emulsifyable liquid concentrate. Such concentrates can be made by dissolving the active ingredient in dimethylsulfoxide, tetrahydrofuran, chloroform, tetrahydrofurfuryl alcohol, acetone, a mixture thereof or a mixture of either of these solvents with small amounts of water, lower alkanols, dimethylformamide, dimethylacetamide or the like. Concentrates should contain between 25 and 50% by weight of the acryloyl ureas.

Sprayable dusts can be prepared from the above ureas using customary dusting powders, e.g., finely divided bentonite, chalk, clay, calcium carbonate, silica, kaoline, talc, fuller's earth, etc. and containing agriculturally acceptable wetting agents, detergents, etc. Solid compositions of this nature can also be prepared in the form of wettable powders which easily disperse in water for spraying. Formulations of this type can be prepared in accordance with PESTICIDE FORMULATIONS by Van Valkenberg (Marcel Dekker, Inc., New York 1973) pp 175–186. Solid formulations preferably contain between 25 and 75% by weight of the shown urea.

In order to illustrate the use for the new compounds of structure I, reference is made to the following examples which are not to be understood as limiting the invention in any form.

EXAMPLE 1

To a mixture of 9.3 g. of acrylamide and 125 ml. of o-dichlorobenzene in a 500 ml. 3-neck flask equipped with thermometer and reflux condenser carrying a drying tube, 25 g. of 4-ethoxycarbonylphenyl isocyanate and 0.1 g. of hydroquinone was added with stirring. The resulting mixture was heated at 150° C. for 90 minutes under stirring. The clear solution was then allowed to cool to room temperature and stand overnight before filtering the formed white crystals. Recrystallization of the 29.8 g. of crude material (88% of theory) from ethanol produced 17.9 g. (53% ) of white, crystalline 1-acryloyl-3-(4-ethoxycarbonylphenyl)urea, m.p. 188°–90° C. The ir and nmr spectra confirmed the assigned structure.

EXAMPLE 2

A mixture of 35.6 g. N-bromosuccinimide, 16.8 g. of alcyl chloride and 0.15 g. of benzoyl peroxide was placed in 125 ml. of chloroform in a 500 ml. 3-neck flask equipped as in Example 1 and heated to reflux for 10 hours at which time a peroxide test was negative. The clear solution was allowed to cool to room temperature. A solution of 33 g. of ethyl 2-aminobenzoate in 150 ml. of chloroform was added to the water bath-cooled solution under stirring. The mixture was then stirred for two hours at room temperature and the formed white crystals representing 30.1 g. of 1-(-bromopropionyl)-3-(2-ethoxycarbonylphenyl)urea, were filtered off; m.p. 182°–6° C.

The above bromopropionylurea (25.9 g.) was heated in 250 ml. of DMF and 75 ml. of triethylamine to reflux for 30 minutes. The mixture was then cooled to room temperature, poured into 1 liter of ice-water, causing the precipitation of a white solid. Filtration produced 13.2 g. (69%) of white 1-acryloyl-3-(2-ethoxycarbonylphenyl)urea. Recrystallization from ethanol/water produced 7.6 g. of the pure material, m.p. 135°–8° C.

EXAMPLES 3–8

The following compounds were prepared according to the above methods:

| Example Number | Method of Example | X | R | m.p.°C. |
| --- | --- | --- | --- | --- |
| 3 | 2 | 4-CN | H | 192°–198° |
| 4 | 1 | 4-$C_2H_5$OCO | $CH_3$ | 100°–101° |
| 5 | 2 | 3-$C_2H_5$OCO | H | 138°–140° |
| 6 | 1 | 4-$CH_3$OCO | H | 210°–211° |
| 7 | 1 | 4-$Me_2$NCO | H | 207°–209° |
| 8 | 1 | 4-$Et_2$NCO | H | 119°–121° |

In the same fashion, the corresponding propyl derivatives and position isomers are made as well as the homologs wherein R is ethyl and propyl. Higher homologs, however, are of lower value as the biocidal activity rapidly decreases from the ethyl- to the propyl-phenyl ureas with the butylphenyl derivatives having essentially no useful fungicidal activity.

EXAMPLES 9

The antifungal properties of the above compounds were established in accordance with the following examples of standard tests:

(A) *Phytophtora infestans* (Late Tomato Blight).

Bonny Test tomato plants, grown to 5-leaf stage in a greenhouse on Swiss Farm potting soil in 7-ounce styrofoam pots with weekly 20-20-20 fertilizer application at 20°-28° C. day and 15°-20° C. night temperature, are treated with a solution or suspension of the fungicide. Both leaf surfaces are sprayed to run-off with a DeVilbiss atomizer at 10 psi. The formulations are prepared by dissolving the fungicide in an acetone-Tween ® 20 mixture and diluting the solution with water to a fungicide concentration of 1000 ppm.

Two days after the plant treatment, a swarmspore suspension (10,000/ml) is sprayed on the lower leaf surface with the above atomizer to a point just before run-off. The plants are then maintained at 100% humidity and 17° C. for 24 hours and subsequently kept under the above greenhouse conditions until symptoms appear. The fungicidal activity is judged by the percent of necrosis of the third, fourth and fifth leaves.

(B) *Pyricularia oryze*.

Rice plants are grown to the same stage and under the same conditions as the tomato plants in (A) except that they are thinned to 3 plants per pot. The solution or suspension of (A) is applied in the same fashion.

Two days after the plant preparation, the plants are inoculated as in (A) but with a spore suspension containing 50,000 spores/ml, and maintained as in (A). The fungicidal activity is measured as the index of number of lesions per fourth leaf/leaf area.

(C) *Puccinia recondita* f. sp. *tritici* (Leaf rust).

The pretreatment is carried out on Yorkster wheat exactly as in (B) except for using the plants in the 1-leaf stage.

Inoculation follows the above method except that the uredospore suspension contains 20,000 spores/ml. and the plants are maintained as above and judged as in (B) on the basal leaf.

The results, expressed as % of protection are shown below: In all tests, the initial 1,000 ppm fungicide solution or suspension is further diluted to determine the activity at 100 and 10 ppm.

| Compound of Example | % Protection for Tests | | | |
|---|---|---|---|---|
| | ppm | A | B | C |
| 1 | 100 | 48 | 90 | 96 |
| 1 | 10 | 5 | 0 | 28 |
| 4 | 100 | 86 | 96 | 0 |
| 4 | 10 | 18 | 68 | 0 |

EXAMPLE 10

In an in vitro test, some of the compounds of formula I was tested in an agar plate minimum inhibitory concentration (MIC) screen from a solution in dimethylformamide against a challenge mixture of Rhizoctonia sp No. 657 and 659. The results are shown in the following table:

| Compound of Example | MIC (ppm) |
|---|---|
| 1 | 10 |
| 2 | 100 |
| 3 | 10 |
| 4 | 10 |
| 5 | 100 |
| 6 | 10 |
| 7 | 1000 |
| 8 | 1000 |

EXAMPLE 11

In an in vitro MIC test, the amount of the test compound of Formula I needed to prevent fungi growth is established. In this test, agar containing the test compound at a specified concentration is inoculated with 1 ml. of a broth containing 10,000 units each of *A. niger* and *P. funiculosum*. The agar plates inoculated in this fashion are incubated at 30° C. for 2 weeks and growth of the microorganisms is visually inspected to establish the MIC. The compounds of Examples 1 and 4 show MIC values of 10 ppm; those of Examples 3 and 5 whos 100 ppm.

EXAMPLE 12

The above compounds can easily be incorporated into a paint formulation according to the following method:
Water—215.9 lbs.
Anionic surfactant—10.5 lbs.
Non-ionic surfactant—2.5 lbs.
Dispersing agent—1.5 lbs.
Hydroxyethylcellulose—2.3 lbs.
Ethylene glycol—25.0 lbs
Defoamer—3.0 lbs.
Titanium dioxide—237.0 lbs.
Fungicide of Compound I—4 lbs./100 gals.

The above ingredients are dispersed for 20 minutes and then blended with a mixture of:
Acrylic emulsion—390.8 lbs.
Long oil alkyd—30.8 lbs.
Cobalt drier—0.2 lbs.
Zirconium drier—0.6 lbs.
Defoamer—1.0 lbs.
Tributylphosphate—9.2 lbs.
Ammonia—1.0 lbs.

EXAMPLE 13

A further test is carried out on tomato plants grown in accordance with Example 9, Test A, using a suspension of 10,000 spores/ml of *Alternaria solani* (early blight) and the plants are then kept at 21° C. and 100% humidity for 24 hours and maintained and observed as in Test A. With the compound of Example 1 at 100 ppm, a 9% necrosis results, while with industry standard Maneb ®, the same concentration results in 10% necrosis. With the compound of Example 4, the results show 11% necrosis with 8% for the control. No injury to the plant is observed in either case.

Although the above examples primarily demonstrate the fungicidal effects of the compounds of Formula I wherein X is ethoxycarbonyl in any of the ring positions of the phenyl moiety, it is noted that when X is cyano, ethylaminocarbonyl or propylaminocarbonyl or the like in any ring position, similar protection of agricultural crops or an industrial substrate is obtained.

As will be seen from the results of the above accelerated fungicidal tests, fabrics, paints, painted surfaces and crops are well protected by compounds of Formula I against the most common fungi. In many instances, the current compounds are superior in their protective quality to the currently used standards in the respective settings; additionally they are environmentally acceptable.

When crops are to be protected with any of the above compounds, the described wettable powder or emulsifiable concentrate is best applied in an aqueous spray containing 0.0001–0.1% by weight of the fungicide, preferably between 0.001 and 0.05%. These compositions may also contain between 0.1 and 5% by weight of a wetting agent, such as an alkyl sulfate, an alkylaryl sulfonate, a sulfosuccinate, a polyethylene glycol ether, or the like. Dusting powders made with the current fungicides and finely divided, inert diluents preferably also contain the fungicide in the above concentration.

For use in paint or other coatings, the above compounds can be added in amounts of 0.01 to 1.0% by weight, preferably between 0.3 and 0.6%. When used in textiles, including cellulosics, wool, synthetics, a stock solution for treating the fabric is best prepared in such a fashion that when the continuously moving woven or nonwoven fabric travels through the bath containing the above compound, it picks up between 0.05 and 1.0% by weight of said compound, calculated on a dried weight. The necessary level of fungicide can thus be added to any of the various solutions that are ordinarily used in the finishing treatment of textiles.

For use as a fungicide in a polymeric material suitable for extruding, molding or foaming, the compound of Formula I is best added to the polymeric powder or to one of the monomer mixes from which the polymer is formed. In these instances, the fungicide is preferably used in such a concentration that the final structure contains between 0.1 and 1.0% by weight thereof.

We claim:

1. The process of protecting substrates against attack by common fungi consisting essentially in applying to said substrates an antifungally effective amount of a compound of the formula

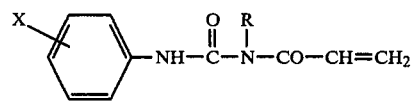

wherein X is, COOalk wherein R is hydrogen or alk, and alk is a loweralkyl of 1–3 carbons.

2. The process of claim 1 wherein said amount is between 10 and 5000 ppm.
3. The process of claim 1 wherein X is ethoxycarbonyl.
4. The process of claim 3 wherein said ethoxycarbonyl is in the p-position.
5. The process of claim 4 wherein R is methyl.
6. The process of claim 4 wherein R is hydrogen.
7. An agricultural antifungal composition containing, as an active ingredient, 0.001–0.5% by wt. of a compound in accordance with claim 1 in an agronomically acceptable diluent.
8. The composition of claim 7 in the form of a water-emulsifyable liquid concentrate.
9. The composition of claim 8 wherein said concentrate uses acetone as the liquid phase.
10. The composition of claim 7 in the form of a wettable powder.
11. A urea of the formula

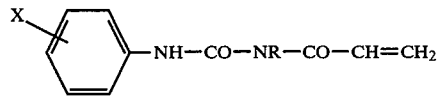

wherein X is COOalk wherein R is hydrogen or alk, and alk stands for an alkyl group of 1–3 carbons.

12. The urea of claim 11 wherein X is ethoxycarbonyl.
13. The urea of claim 12 wherein said X is in the p-position.
14. The urea of claim 13 wherein R is hydrogen.
15. The urea of claim 13 wherein R is methyl.

* * * * *